(12) United States Patent
Gardner (10) Patent No.: US 6,427,254 B1
(45) Date of Patent: Aug. 6, 2002

(54) EYE PROTECTION DEVICE

(76) Inventor: Lawrence C. Gardner, 24 Elliott Rd., Sterling, MA (US) 01564

( * ) Notice: Subject to any disclaimer, the term of this patent is extended or adjusted under 35 U.S.C. 154(b) by 0 days.

(21) Appl. No.: 09/802,557

(22) Filed: Mar. 12, 2001

(51) Int. Cl.[7] ................................................. A61F 9/02
(52) U.S. Cl. ......................................... 2/444; 351/158
(58) Field of Search ............................ 2/444, 431, 435, 2/411, 414, 425, 426, 433, 434, 439, 440, 443; 351/44, 158, 62, 83, 155

(56) References Cited

U.S. PATENT DOCUMENTS 5,144,344 A * 9/1992 Takahashi et al. ............ 351/44
5,339,119 A * 8/1994 Gardner ...................... 351/158
6,062,688 A * 5/2000 Vinas .......................... 351/47

* cited by examiner

Primary Examiner—Peter Nerbun
Assistant Examiner—Katherine Moran
(74) Attorney, Agent, or Firm—William Nitkin (57) ABSTRACT

Disclosed is an eye protection device for the enclosure of eyeglasses therein, such device having a resilient cushion member which extends rearwardly therefrom to form an upper portion and a lower portion and first and second sides, such device having lens openings provided in the cushion member, with the wearer's eyeglasses fitting within grooves and a bridge slot formed within such cushion member, such device having hard side members attached to the first and second sides of the cushion member, and with such resilient cushion member's upper and lower portions and first and second sides contacting the wearer's face.

21 Claims, 9 Drawing Sheets

EYE PROTECTION DEVICE

BACKGROUND OF THE INVENTION

1. Field of the Invention

The device of this invention resides in the area of eye protection devices and more particularly relates to an eyeglass frame holder which receives a pair of eyeglasses therein and acts as a protective shield around the eyeglasses and the area between the eyeglasses and the wearer's face.

2. Description of the Prior Art

Protective eye wear, such as ski goggles and safety goggles, are well known in the prior art. In this field the inventor herein has been granted U.S. Pat. No. 5,339,119 for an Eye Protection Device Comprising a Foam Rubber-like Resilient Insert Member in Aug. 16, 1994. In the device of Pat. No. 5,339,119 the wearer's eyeglasses are surrounded by a foam-like resilient member having channels to receive the eyeglass frame securely therein.

SUMMARY OF THE INVENTION

It is an object of this invention to provide improvements over my prior device in order to better receive and retain eye wear of various shapes within the device of this invention and to provide improved means of retaining the ear pieces of the eye wear therein.

It is a further goal of this invention to provide improved peripheral vision by the utilization of clear or clear tinted hard plastic side shields disposed as part of the device through which the wearer can exercise peripheral vision. It is still a further goal to meet the Occupational Safety and Health Act Personal Protective Equipment (PPE) specifications and requirements to block airborne blood pathogens by means of safety goggles that have solid side shields.

It is yet a further goal of this invention to provide a more attractive and therefore, more desirable, eye protection device than that available in the prior art.

DESCRIPTION OF THE PREFERRED EMBODIMENT(S)

Figure 1:
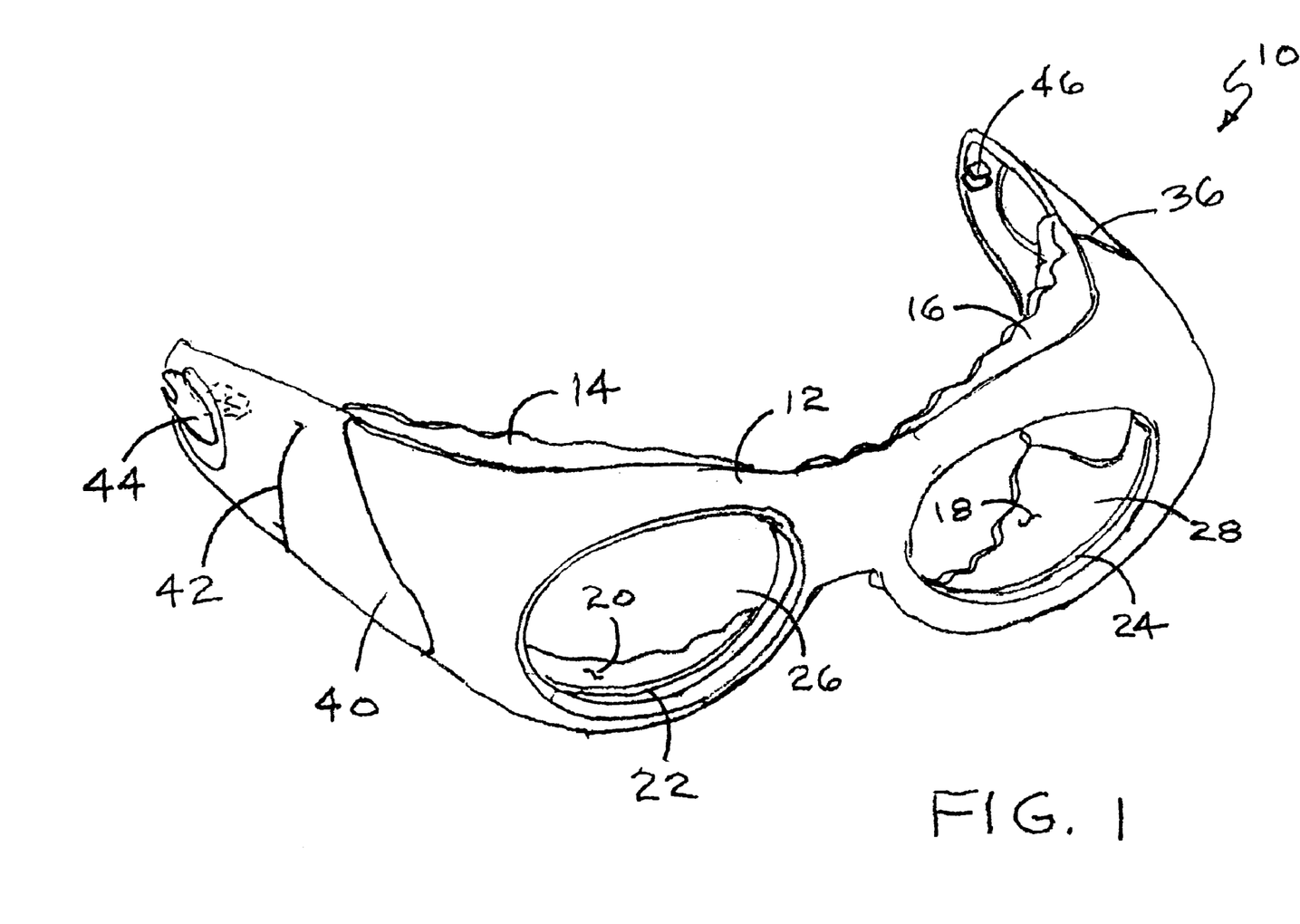
FIG. 1 illustrates a front perspective view of the Eye Protection Device of this invention.
Figure 2:
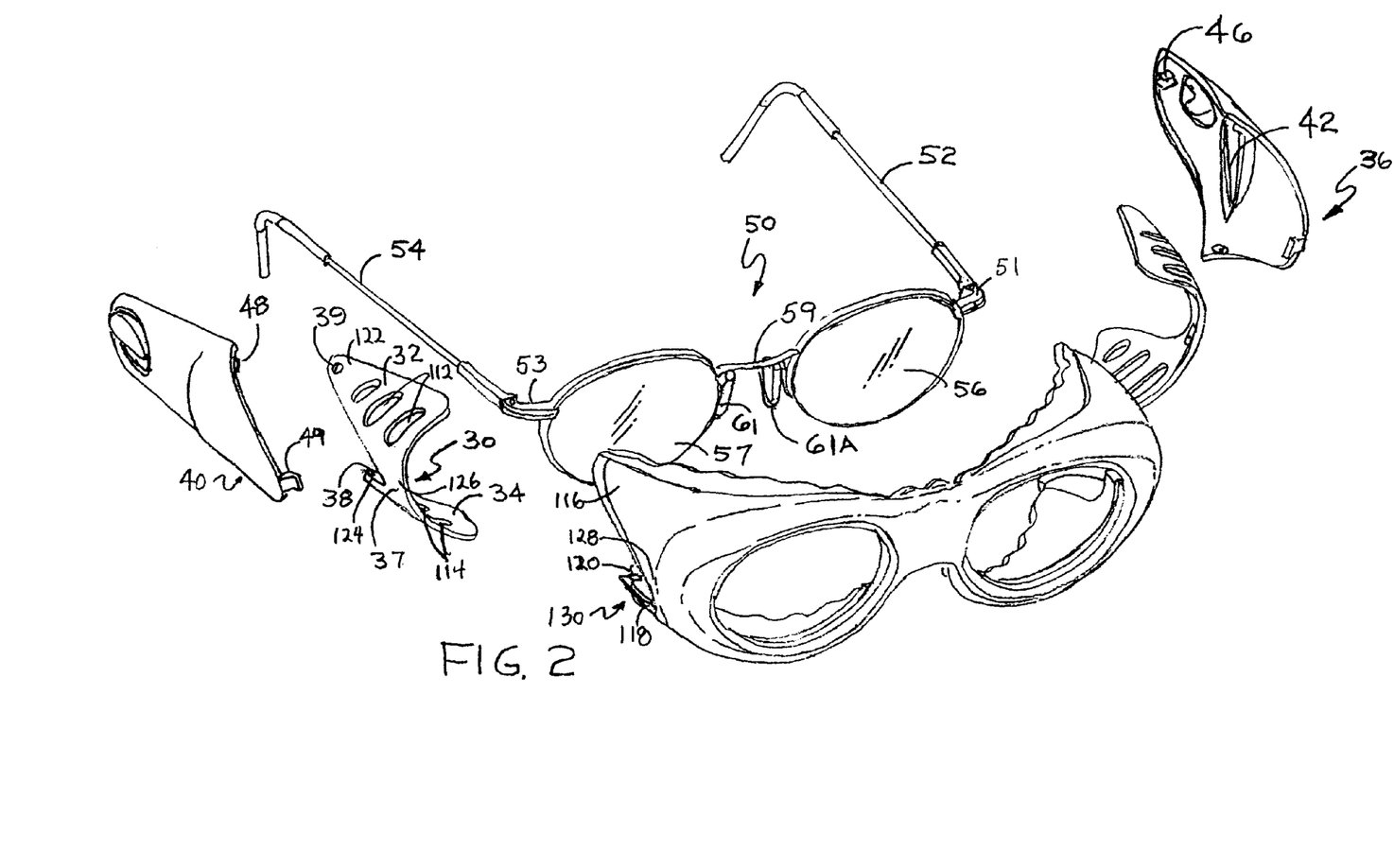
FIG. 2 illustrates a front perspective view of the Eye Protection Device of this invention with the side member components shown separated therefrom and the eye wear shown disposed to the rear thereof
Figure 3:
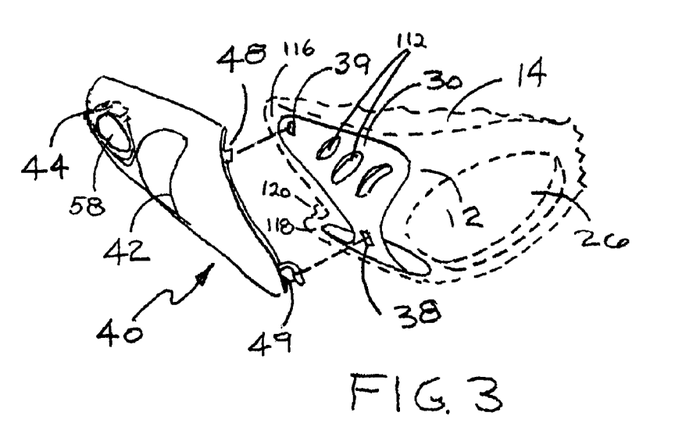
FIG. 3 illustrates a side perspective view of the Eye Protection Device of this invention showing the internal and external portions of a hard side member, with such portions shown separated from one another and with a portion of the resilient materials shown in dashed lines.
Figure 4:
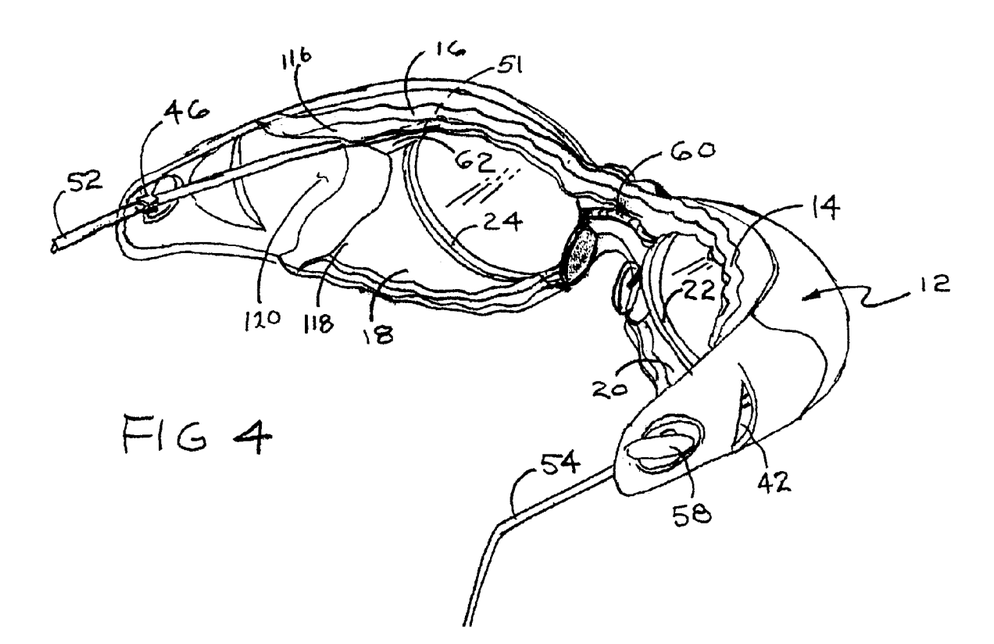
FIG. 4 illustrates a rear perspective view of the device of this invention shown with a pair of eyeglasses inserted therein.
Figure 5:
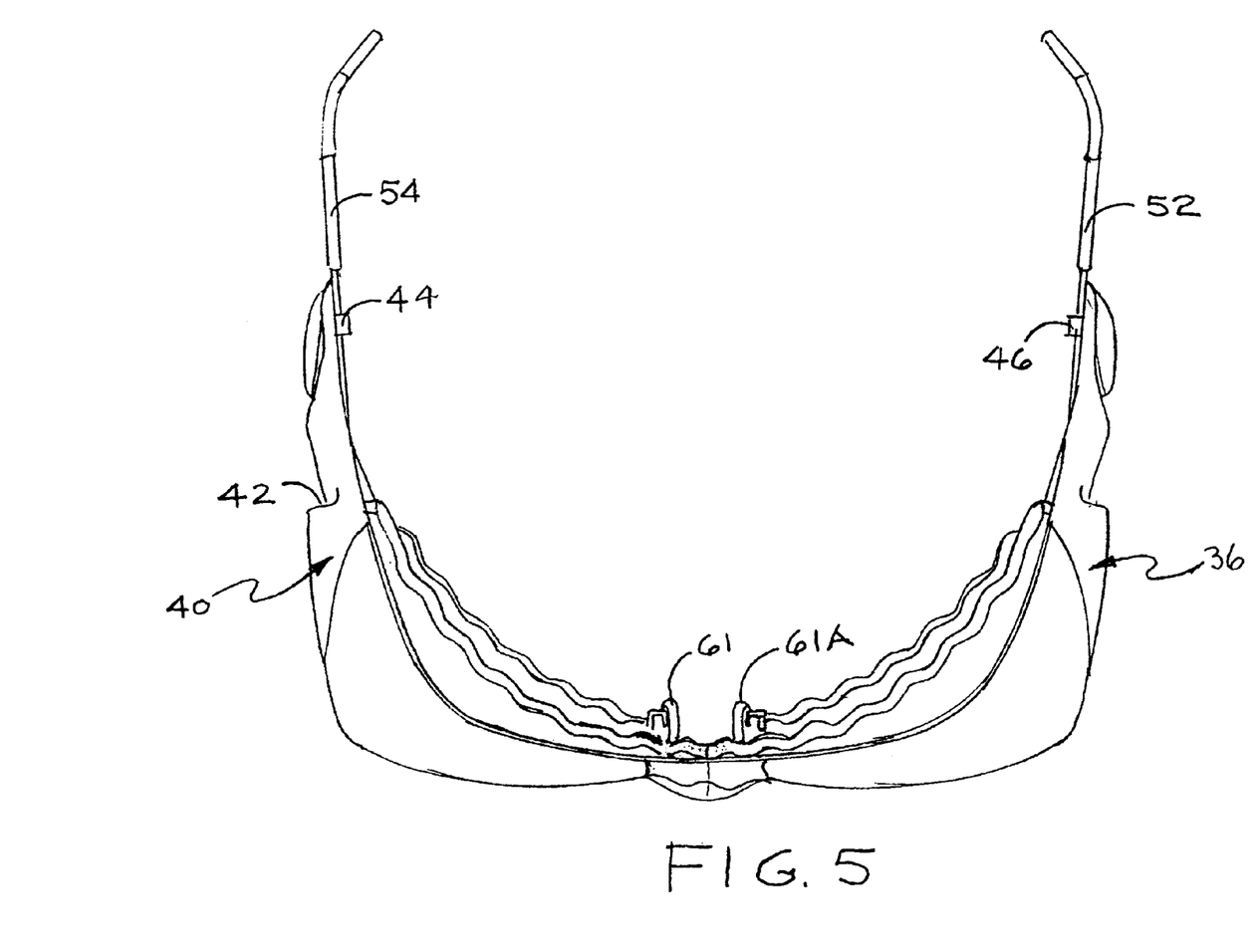
FIG. 5 illustrates a top plan view of the device of this invention with the eye wear inserted therein.

The device of this invention is a substantially soft, resilient structure with rigid portions, as described further below. The eye wear is received within eyeglass receipt channels that are formed in the device. The eye wear can be prescription or nonprescription eye wear including sunglasses and wraparound sports glasses. The device of this invention not only surrounds and retains the eyeglasses, but also extends rearward from the lenses to contact the wearer's face to provide a barrier for the wearer's eyes against the elements such as wind as well as to prevent any airborne particles from reaching the wearer's eyes. Air circulation vents are provided to minimize fogging of the lenses. The air vents are contoured directionally so that in some embodiments they face rearwards so that, for example, airborne particles such as blood borne pathogens cannot enter the eye cavity from a frontal direction. In other embodiments, for example in sports usage such as skiing, the air vents can be forwardly directed to receive fresh air flow so as to minimize lens fogging. In certain embodiments the air vents can be adjustable to face in either direction. The structure 10, as seen in the front perspective view of FIG. 1, can be formed of a more rigid outer front shell 12 in which is positioned a more resilient foam rubber-like cushion member, as described further below. The device of this invention can be worn not only in sporting environments, but also worn in other environments as safety glasses. Seen in FIG. 1 extending rearwards from front shell 12 is an upper cushion member formed of first cushioning member 14 and contiguous second cushioning member 16 which form a unitary piece attached to and extending to the rear of front shell 12 around first eyeglass aperture 26 and second eyeglass aperture 28 over the bridge of the nose as well as extending rearward at the bottom of the structure to form second lower cushioning member 18 and contiguous first lower cushioning member 20. Within first eyeglass aperture 26 and second eyeglass aperture 28 are, respectively, first groove 22 and second groove 24. As seen in FIG. 4, extending between first groove 22 and second groove 24 is bridge slot 60 designed for the receipt of bridge 59, as seen in FIG. 2, of eyeglasses 50 when second eyeglass 56 and first eyeglass 57 are engaged into second groove 24 and first groove 22, respectively. At the same time second and first eyeglass ear piece hinges 51 and 53 are received, respectively, into their second and first hinge slots, such as second ear piece hinge 51 into second hinge slot 62, as best seen in FIGS. 4 and 5. The resiliency of the cushioning material in which all of the grooves and slots are formed causes such material to urge snugly around the eyeglass frame and hold it securely in position to form a wind and watertight seal therearound. The resilient cushioning material then extends rearward from front shell 12, as cushioning members described above, to urge against the wearer's forehead and cheeks to further form a wind and fluid-tight seal thereagainst. The rearwardly extending upper and lower cushioning members 14, 16, 18 and 20 can be scalloped, as shown, to better and more easily compress against the wearer's face. The resilient cushioning material can be made of a soft, resilient urethane foam or equivalent material. The resilient cushioning material then provides a form of impact protection during sports activities, such as soccer, basketball, and football where a blow to the face of one wearing other types of eye wear might push the eye wear into the face, causing cuts. The foam nature of the resilient cushioning material, having air trapped therein and floatable in water, allows an individual wearing the device of this invention who is engaged in water sports the additional security of having the device of this invention act as a flotation means for his eye wear should it get knocked off while that individual is in the water or engaged in water sports such as boating or jet skiing. First and second ear pieces 54 and 52 of eyeglasses 50 are retained, respectively, within first and second ear piece attachments 44 and 46, as seen in FIGS. 1 and 4. First and second ear piece attachments 44 and 46 are formed, respectively, within first and second hard side members 40 and 36. Each hard side member can include an air vent, such as air vent 42. To retain first and second hard side members 40 and 36 to their respective rearwardly extending, more easily tearable, foam cushioning member, an insert member, such as first hard insert member 30, is inserted during manufacture and molded into each side of the rearwardly extending foam-like cushioning members such as best seen in FIG. 3. The hard side members form side shields can be made of clear, tinted, opaque or even mirror-surfaced material for many different uses such as in sporting activities or in medical safety environments.

In FIG. 3 one can see first eyeglass aperture 26, the first portion of front shell 12 and a portion of first upper cushioning member 14 all depicted in dashed lines surrounding first hard insert member 30 which is molded therein and which member conforms to the general shape of the side of the cushioning members. First hard side member 40 has a plurality of small extension members such as upper extension member 48 and mid-extension member 49 which can be engaged, respectively, through the foam material into upper insert receipt notch 39 and mid-insert receipt notch 38 defined in first hard insert member 30 so that first hard side member 40 can be engaged thereto and locked in position during construction of the device of this invention. A lower extension member and mating receipt notch can also be provided at the bottoms of first hard side member 40 and first hard insert member 30 but are not seen in this view. Because of the difficulty of attaching a hard member to an easily tearable foam member, first hard insert member 30 is utilized. In the embodiment of FIG. 3, first hard insert member 30 is shown with a plurality of upper insert apertures 112 which are positioned along its upper portion. Not seen in this view are a plurality of lower insert apertures 114 formed in its lower portion but which can be seen in FIG. 2. The rearwardly extending side 130 of the foam is formed of an upper protrusion 116 and a lower protrusion 118 which have an open, notch-like area 120 defined therebetween. The thin curved first hard insert member 30 is also formed with an upper protruding second portion 122 and a lower protruding second portion 124 which are encased within the foam of upper protrusion 116 and lower protrusion 118, respectively, with the central portion 126 of hard insert member 30 embedded within the central side portion 128 of side 130 of the foam cushion member. The foam passes through upper insert apertures 112 and lower insert apertures 114 to securely lock first hard insert member 30 in position when it is molded in place within side 130 of the foam member. In this way the curved body of first hard insert member 30 is positioned and adds strength to side 130 of the foam cushion member and forms a secure base for the attachment of first hard side member 40 thereto when the attachment members, such as attachment members 48 and 49 are engaged into receipt notches such as receipt notches 39 and 38, respectively. First hard side member 40 can have a similar streamlined shape to the curved open area 120 which it covers when it is securely attached to side 130 of the foam. In this way, by utilizing a hard insert member, the side members, such as first hard side member 40, can be securely attached to the resilient foam cushioning material so that each side of the device where it attaches to an ear piece can be more firm and thus provide for a more secure attachment. Hooks, such as hook 58 seen in FIG. 4, can be provided on the rear outer side of each side member for attaching straps thereto which can extend around the wearer's head. Such straps to hold eyeglasses are not illustrated but are well known.

Figure 6:
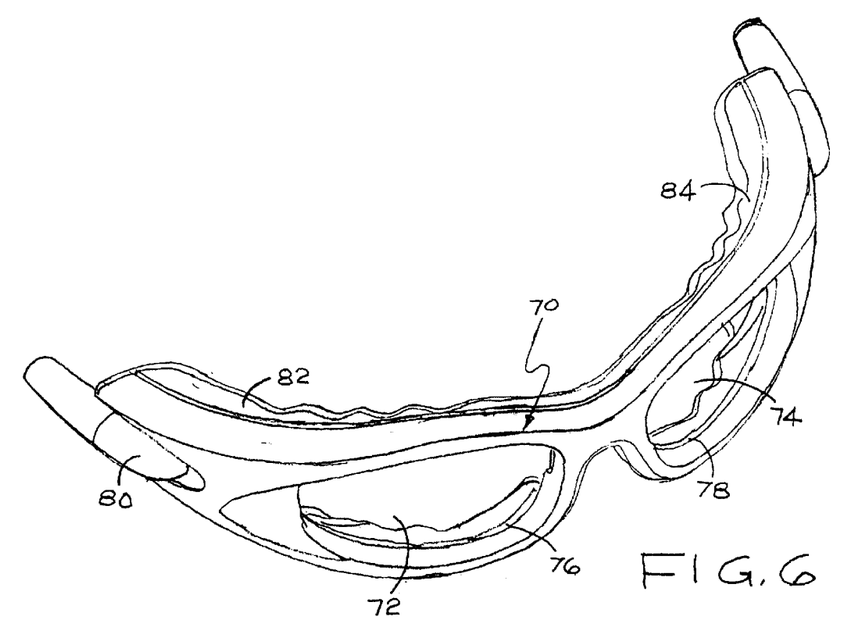
FIG. 6 illustrates a perspective view of an elongated wraparound version of the Eye Protection Device of this invention having an alternate ear piece retention structure for use with sports eye wear.
Figures 7, 7A:
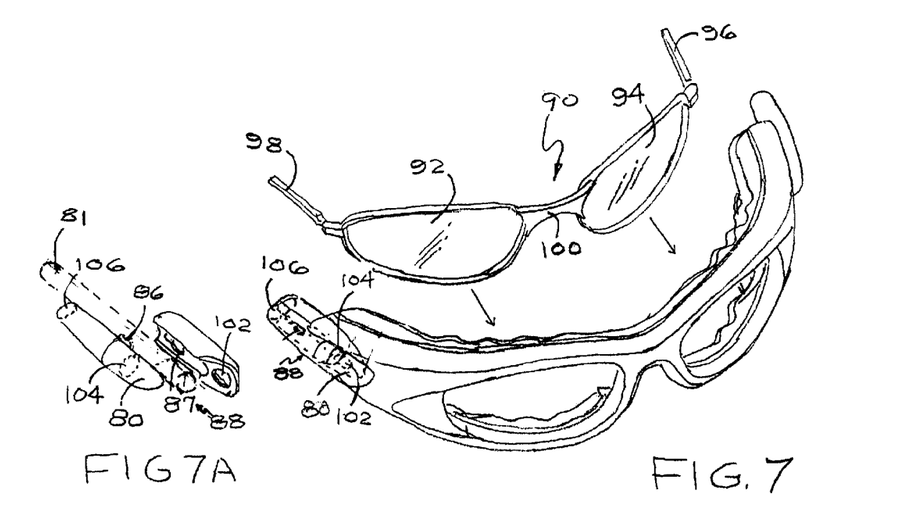
FIG. 7 illustrates a perspective view of the Eye Protection Device of FIG. 6 showing the ear piece retention member and the sports eye wear disposed to the rear thereof.
FIG. 7a illustrates a perspective exploded view of the ear piece retention member of FIG. 7 shown removed from the resilient foam and the ear piece receipt member separated therefrom.
Figure 8:
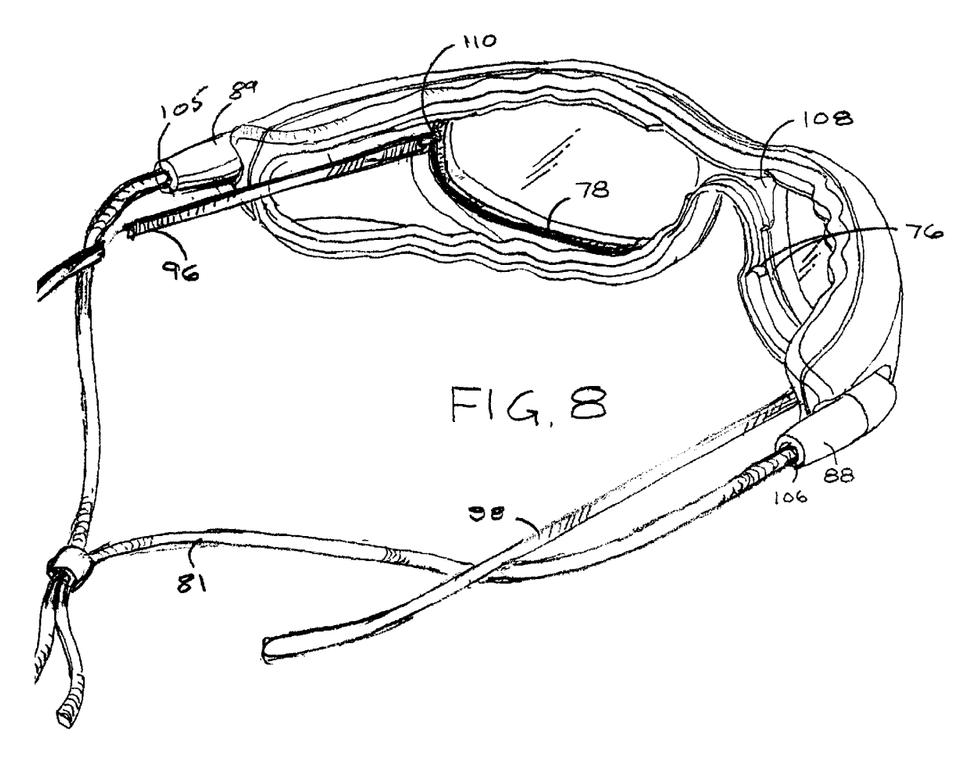
FIG. 8 illustrates a rear perspective view of the Eye Protection Device of FIG. 6 showing the eye wear inserted therein.

FIG. 6 illustrates an embodiment of this invention that can be utilized with wraparound-style eyeglasses 90, as seen in FIG. 7. In this embodiment first and second openings 72 and 74 to receive wraparound eyeglasses 90 are laterally elongated and function in substantially the same way as the embodiment of FIG. 2 discussed above. Since the wraparound eye wear curves closer to the face of the wearer, the rearwardly extending first and second compression members 82 and 84 are not as deep as their counterparts first and second upper cushioning members 14 and 16. They still extend to, and contact, the face of the wearer both above and below the wraparound eyeglasses. In this wraparound version a different ear piece retention system is utilized. As seen in FIG. 7 the wraparound eyeglasses have a first lens 92 and second lens 94 joined by bridge 100 with rearwardly extending first and second ear pieces 98 and 96. First strap retention member 88, seen in FIG. 7a, can be attached to the side of the foam of the elongated version and has, for example, a strap aperture 102 provided therein for receipt therein of strap 81 which then passes through channel 104 and out exit 106 in first strap receipt member 80 which can be attached to first strap retention member 88 by engaging catch member 86 formed as part of first strap receipt member 80 into retention member slot 87 formed in the first strap retention member 88. First and second ear pieces 98 and 96 extend on the inside of the strap retention members within and beyond the cushion structure of this invention, as seen in FIG. 8. The completed device containing a pair of wraparound eyeglasses can be seen in FIG. 8 where strap 81 is seen passing out from first and second strap exits 106 and 105 of first and second strap retention members 88 and 89, respectively.

Figure 9:
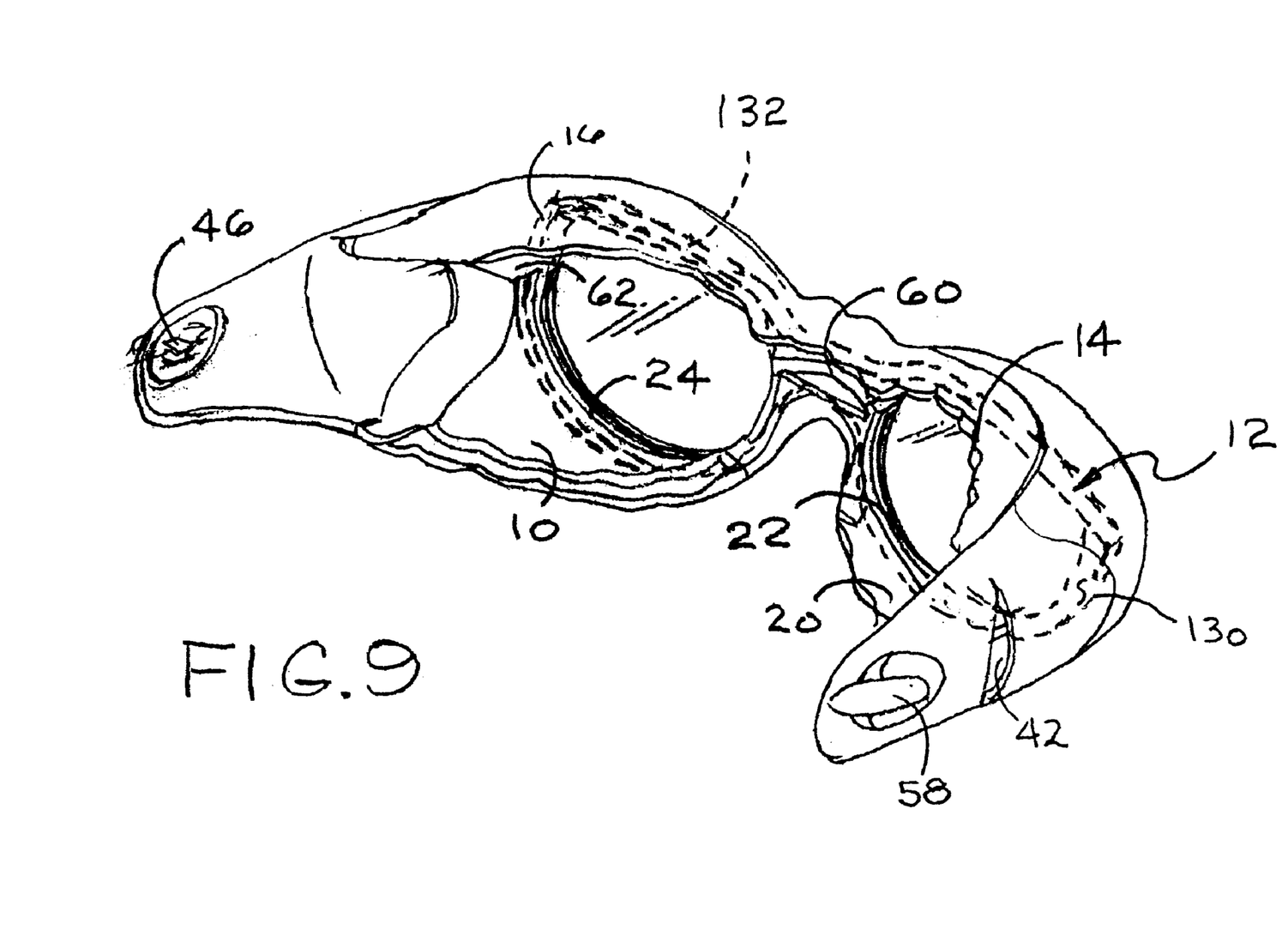
FIG. 9 illustrates a rear perspective view of the Eye Protection Device of FIG. 1 utilized with an eyeglass frame having no ear pieces.

FIG. 9 illustrates an alternate embodiment of the invention utilizing a modified eyeglass frame 132 without ear pieces which has been fitted within first and second grooves 22 and 24 and bridge slot 60 of structure 10. The eyeglasses can be purchased in this style without ear pieces to be lighter in weight and less expensive. Such eyeglass frames will work well in all the embodiments of this invention, such as the version of FIG. 1 and the version of FIG. 6.

Although the present invention has been described herein as having a substantially rigid front shell, it must be considered part of this invention that the entire structure of the Eye Protection Device can be molded from the same material at one time, thus being a single piece rather than made up of discrete elements. When molded of a unitary piece of foam-like material, the distinguishing form and shape of the front shell member can be painted by an "in the mold" painting process which process is well known and has the capability of producing multiple color combinations.

Figure 10:
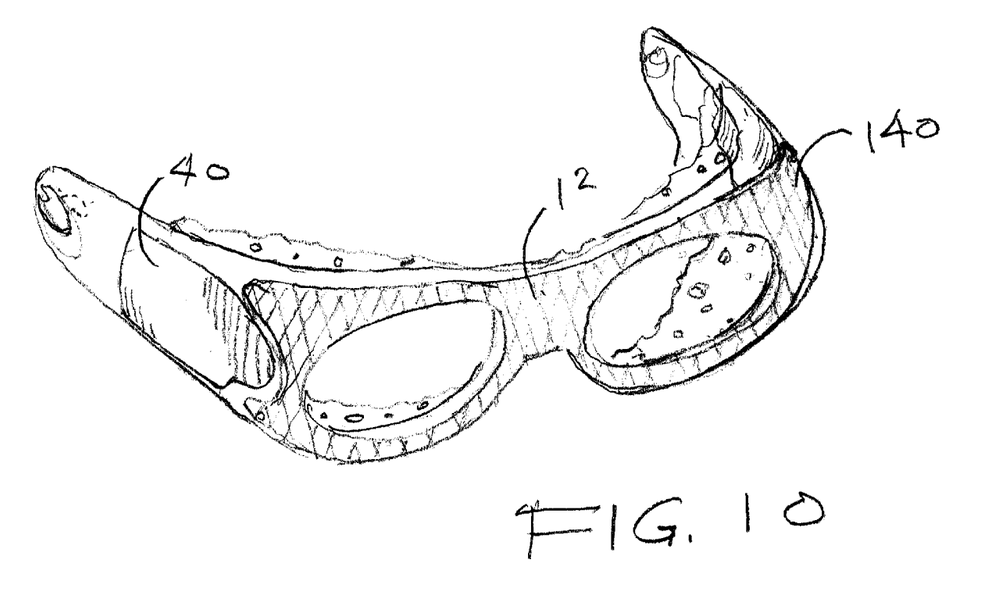
FIG. 10 illustrates a front perspective view of the Eye Protection Device of this invention molded around an internal web structure.

FIG. 10 illustrates a front perspective view of the Eye Protection Device of this invention having a stiffening web 140 formed generally within its molded structure. Web 140 can be of a harder mesh plastic material placed within a mold in which the foam is poured and which passes through and around the web material. The Eye Protection Device of this invention would otherwise look and function the same as previously described but would have the advantage in some situations of the additional strength that the internal web would provide thereto especially around the nose and bridge areas of the device.

Figure 11:
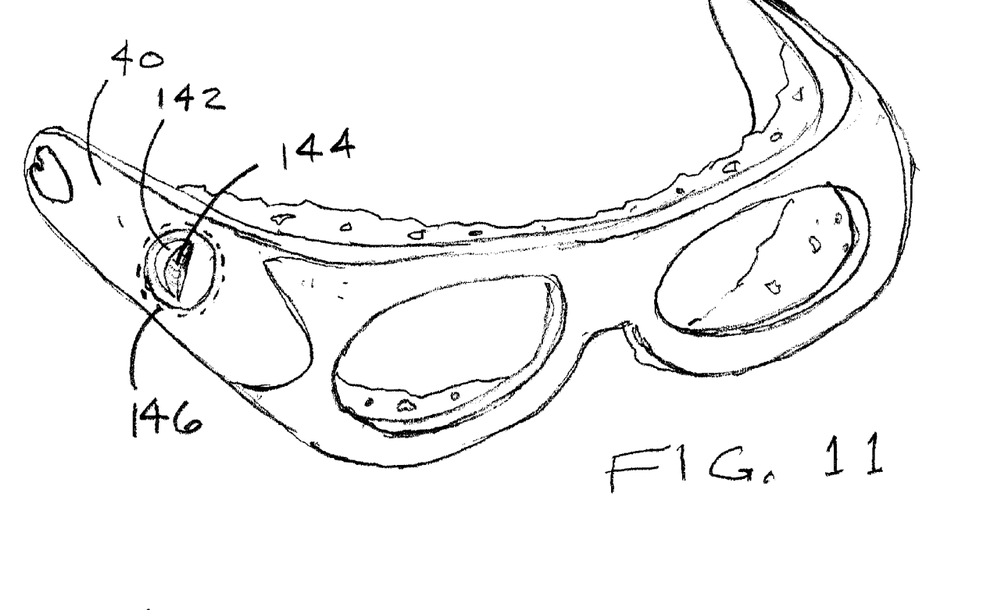
FIG. 11 illustrates a front perspective view of the Eye Protection Device of this invention incorporating an adjustable-direction air vent.

FIG. 11 illustrates an embodiment of the Eye Protection Device of this invention having an adjustable, positionable air vent 142. As seen in FIG. 11, air vent 142 has its opening 144 disposed frontward. In this embodiment air vent 142 is rotatable, being round and disposed rotatably within a round aperture defined in side member 40.

Figure 12:
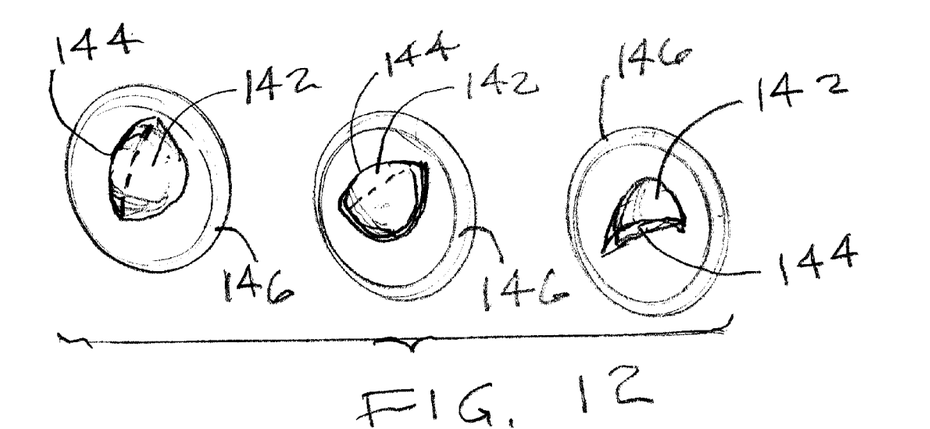
FIG. 12 illustrates a perspective view of a rotatable air vent shown rotated in three different positions.

FIG. 12 shows, by rotating air vent 142, that air vent opening 144 can be disposed in other directions including rearwards as seen in the leftmost example of this figure. In this way air vent 142 can be directionally adjustable. Air vent opening 144 can form an air scoop and be rotated within round opening 146 to any desired direction. Other equivalent means of changing the direction of the air vent could be utilized.

Although the present invention has been described with reference to particular embodiments, it will be apparent to those skilled in the art that variations and modifications can be substituted therefore without departing from the principles and spirit of the invention.

I claim:

1. An eye protection device to be worn on the face of a person wearing eyeglasses, said eyeglasses having ear pieces, comprising:

a resilient member having a front and rear, first and second lens openings defined therein, and first and second sides, said resilient member having a rearwardly extending upper portion and a rearwardly extending lower portion, said upper and lower portions of said resilient member acting as cushion members contacting the face of said wearer, said lens openings having a first groove defined around said first lens opening and a second groove defined around said second lens opening with a bridge slot defined therebetween contiguous with said first and second grooves, said grooves and slot for receiving and retaining said eyeglasses of said wearer therein;

means to retain said ear pieces of said eyeglasses to said rearwardly extending first and second sides of said resilient member; and first and second hard side members, said first and second hard side members affixed, respectively, to said first and second sides of said resilient member.

2. The device of claim 1 further including:

first and second receipt notches defined, respectively, in said first and second sides of said resilient member to receive said first and second hard side members; and said first and second hard side members further including means to releasably retain said ear pieces of said eyeglasses.

3. The device of claim 2 wherein said first and second hard side members include:

first and second hard insert members positioned, respectively, within said first and second sides of said resilient member;

said first and second hard side members positioned, respectively, on said first and second sides of said resilient member; and means to attach said first and second hard side members, respectively, to said first and second hard insert members.

4. The device of claim 3 further including an air vent defined in each of said hard side member.

5. The device of claim 4 wherein said air vent is adjustable in its direction.

6. The device of claim 1 wherein said first and second hard side members have means to retain a strap member.

7. An eye protection device to be worn on the face of a person wearing eyeglasses, comprising:

a resilient cushion member having a front and rear and first and second sides, first and second lens openings defined therein, said cushion member having a rearwardly extending upper portion and a rearwardly extending lower portion, said upper and lower portions of said cushion member contacting the face of said wearer, said lens openings in said cushion member having a first groove defined around said first lens opening and a second groove defined around said second lens opening with a bridge slot defined therebetween contiguous with said first and second grooves, said grooves and slot for receiving and retaining said eyeglasses of said wearer therein; and first and second hard side members, said first and second hard side members affixed, respectively, to said first and second sides of said resilient cushion member.

8. The device of claim 7 further including:

first and second receipt notches defined, respectively, in said first and second sides of said cushion member to receive said first and second hard side members.

9. The device of claim 8 wherein said first and second hard side members include:

first and second hard insert members positioned, respectively, within said first and second sides of said cushion member;

said first and second hard side members positioned, respectively, on said first and second sides of said cushion member; and means to attach said first and second hard side members, respectively, to said first and second insert members.

10. The device of claim 9 wherein said first and second hard side members have means to retain a strap member.

11. The device of claim 9 further including first and second vents defined, respectively, in said first and second hard side members.

12. An eye protection device to be worn on the face of a person wearing eyeglasses, said eyeglasses having ear pieces, comprising:

a substantially rigid front shell member having a front, a rear and first and second lens openings defined therein;

a resilient cushion member having a front and rear and first and second sides, said front of said cushion member positioned within, and attached to, said rear of said shell member, said cushion member having first and second lens openings defined therein aligned, respectively, with said first and second lens openings in said shell member, said cushion member having a rearwardly extending upper portion and a rearwardly extending lower portion, said upper and lower portions of said cushion member contacting the face of said wearer, said lens openings in said cushion member having a first groove defined around said first lens opening and a second groove defined around said second lens opening with a bridge slot defined therebetween contiguous with said first and second grooves, said grooves and slot for receiving and retaining said eyeglasses of said wearer therein; and means to retain said ear pieces of said eyeglasses to said rearwardly extending first and second sides of said cushion member.

13. The device of claim 12 further including:

first and second hard side members, said first and second hard side members affixed, respectively, to said first and second sides of said resilient cushion member.

14. The device of claim 13 further including:

first and second receipt notches defined, respectively, in said first and second sides of said cushion member to receive said first and second hard side members; and said first and second hard side members further including means to releasably retain said ear pieces of said eyeglasses.

15. The device of claim 13 wherein said first and second hard side members include:

first and second hard insert members positioned, respectively, within said first and second sides of said cushion member;

said first and second hard side members positioned, respectively, on said first and second sides of said cushion member; and means to attach said first and second hard side members, respectively, to said first and second hard insert members.

16. The device of claim 12 wherein said first and second hard side members have means to retain a strap member.

17. An eye protection device to be worn on the face of a person wearing eyeglasses, comprising:

a substantially rigid front shell member having a front, a rear and first and second lens openings defined therein;

a resilient cushion member having a front and rear and first and second sides, said front of said cushion member positioned within, and attached to, said rear of said shell member, said cushion member having first and second lens openings defined therein aligned, respectively, with said first and second lens openings in said shell member, said cushion member having a rearwardly extending upper portion and a rearwardly extending lower portion, said upper and lower portions of said cushion member contacting the face of said wearer, said lens openings in said cushion member having a first groove defined around said first lens opening and a second groove defined around said second lens opening with a bridge slot defined therebetween contiguous with said first and second grooves, said grooves and slot for receiving and retaining said eyeglasses of said wearer therein.

18. The device of claim 17 further including:

first and second hard side members, said first and second hard side members affixed, respectively, to said first and second sides of said resilient cushion member.

19. The device of claim 18 further including:

first and second receipt notches defined, respectively, in said first and second sides of said cushion member to receive said first and second hard side members.

20. The device of claim 19 wherein said first and second hard side members include:

first and second hard insert members positioned, respectively, within said first and second sides of said cushion member;

said first and second hard side members positioned, respectively, on said first and second sides of said cushion member; and means to attach said first and second hard side members, respectively, to said first and second insert members.

21. The device of claim 17 wherein said first and second hard side members have means to retain a strap member.

* * * * *